United States Patent
Wiedemann

[11] Patent Number: 6,010,684
[45] Date of Patent: Jan. 4, 2000

[54] REMINERALISING COMPOSITION

[75] Inventor: Wolfgang Wiedemann, Hochberg, Germany

[73] Assignee: SmithKline Beecham Consumer Healthcare GmbH, Buhl, Germany

[21] Appl. No.: 09/254,643

[22] PCT Filed: Aug. 29, 1997

[86] PCT No.: PCT/EP97/04887

§ 371 Date: May 27, 1999

§ 102(e) Date: May 27, 1999

[87] PCT Pub. No.: WO98/10736

PCT Pub. Date: Mar. 19, 1998

[30] Foreign Application Priority Data

Sep. 12, 1996 [GB] United Kingdom ................. 96306639

[51] Int. Cl.$^7$ ............................ A61K 7/18; A61K 33/42
[52] U.S. Cl. ............................................ 424/52; 424/602
[58] Field of Search ...................................... 424/52, 602

[56] References Cited

FOREIGN PATENT DOCUMENTS

| 0 251 591 | 1/1988 | European Pat. Off. . |
| 0 428 492 | 5/1991 | European Pat. Off. . |
| 19 60 068 | 10/1970 | Germany . |
| WO 96 20693 | 7/1996 | WIPO . |

*Primary Examiner*—Raymond Henley, III
*Attorney, Agent, or Firm*—Nora Stein-Fernandez; Janice E. Willimas; Charles M. Kinzig

[57] ABSTRACT

Two phase remineralizing compositions are described comprising a source of calcium ions and a source of phosphate ions together with a water soluble polyphosphate salt.

13 Claims, No Drawings

REMINERALISING COMPOSITION

This is a 371 of PCT/EP97/04887 filed Aug. 29, 1997.

The present invention relates to oral hygiene compositions, in particular remineralising compositions comprising a source of calcium ions and a source of phosphate ions. Such compositions are of use in the prophylaxis and treatment of caries and/or sensitivity.

In a first aspect the present invention provides a remineralising composition comprising:
a) as a first component an aqueous calcium phase comprising a water-soluble calcium salt providing from 0.05 to 10%, by weight of the calcium phase, of calcium ions, and
b) as a second component an aqueous phosphate phase comprising a stabilising amount of a polyphosphate salt and a water-soluble phosphate salt providing from 0.05 to 10%, by weight of the phosphate phase, of phosphate ions;
the two phases being kept separate until use, whereupon on mixing they provide a single phase having a pH from 2.0 to 5.0 and a molar ratio of calcium ions to phosphate ions of from 0.5:1 to 5:1 capable of remineralising teeth.

The compositions of the present invention have the advantage of forcing deep remineralisation and thus are expected to be of use in the prophylaxis and treatment of caries and/or sensitivity. In use, calcium and phosphate ions remain soluble, by virtue of the initial pH of the applied compositions, and can diffuse deeply within carious lesions and/or dentinal tubules. As the pH rises within a tooth, for example by the subsequent action of saliva, precipitation of calcium phosphate occurs resulting in deep remineralisation.

Suitably the calcium salt provides from 1 to 5%, preferably from 2 to 3%, by weight of the calcium phase, of calcium ions. Suitable examples of calcium salts include calcium acetate, calcium formate, calcium lactate, calcium nitrate and mixtures thereof, and preferably, is calcium chloride or a mixture of calcium chloride and calcium lactate.

Suitably the phosphate salt provides from 1 to 5%, preferably from 2 to 3%, by weight of the phosphate phase, of phosphate ions.

Suitable examples of phosphate salts include disodium hydrogen phosphate, potassium dihydrogen phosphate, trisodium phosphate and, preferably, sodium dihydrogen phosphate.

It is important that the phosphate phase comprises a stabilising amount of a polyphosphate salt which improves the long term storage stability and efficacy of the remineralising composition.

Suitably the polyphosphate salt is an alkali metal pyrophosphate or tripolyphosphate. Preferably it is an alkali metal polymetaphosphate for example sodium polymetaphosphate (otherwise known as Graham's salt or sodium hexametaphosphate).

Suitably the polyphosphate salt is present up to 250 ppm, preferably from 5 to 200 ppm, most preferably from 5 to 20 ppm, by weight of the phosphate phase.

The pH of the calcium and phosphate phases are such that on mixing they result in a pH from 2.0 to 5.0, preferably 3.0 to 4.5, more preferably 3.5 to 4.0, most preferably 3.5 to 3.8.

Conveniently equal amounts, by weight, of the calcium and phosphate phases are mixed prior to use.

Suitably the pH of the calcium phase is from 3.0 to 7.0, preferably 3.0 to 6.0.

Suitably the pH of the phosphate phase is from 3.0 to 6.5, preferably 3.5 to 6.0.

The molar ratio of calcium ions to phosphate ions should be such to ensure effective remineralisation of teeth. Suitably the molar ratio of calcium ions to phosphate ions is from 1:1 to 3:1, eg 2:1.

Advantageously the composition of the present invention comprises in the phosphate phase a source of fluoride ions, such as an alkali metal fluoride (eg sodium fluoride), an amine fluoride or an alkali metal monofluorophosphate (eg sodium monofluorophosphate).

The presence of fluoride ions helps the permanent precipitation of calcium phosphate as hydroxyapatite during the remineralisation process.

Suitably the composition comprises from 50 to 2500 ppm of fluoride ions, eg from 100 to 1500 ppm of fluoride ions by weight of the total composition.

Alternatively the composition comprises a catalytic amount of fluoride ions, preferably from sodium fluoride, eg up to 50 ppm, suitably up to 20 ppm, preferably between 1 and 10 ppm, most preferably between 4 and 6 ppm of fluoride ions, by weight of the total composition.

Suitable compositions of the present invention include rinses, gels or dentifrices, providing that the calcium and phosphate phases are kept separate until use.

For example such compositions can be packaged into a container such as bottle or tube having two chambers for separating each phase, the container having a dispensing nozzle allowing controlled dispensing and preferably concomitant mixing of said phases prior to use. Alternatively such compositions can be packaged into a sachet having two chambers separated by a frangible seal which can be ruptured prior to use allowing mixing of the calcium and phosphate phases within the sachet.

The calcium and phosphate phases may also be packaged in separate containers which can dispense the required amount of each phase prior to mixing and use. The present invention therefore also provides a kit comprising separately packaged calcium and phosphate phases as hereinbefore defined, which on mixing provide a single phase capable of remineralising teeth.

Compositions of the present invention will contain appropriate formulating agents such as abrasives, surfactants, humectants, thickening agents, flavouring agents, sweetening agents, opacifying or colouring agents, preservatives and water, selected from those conventionally used in the oral hygiene composition art for such purposes and which are compatible with the calcium and phosphate phases hereinbefore described.

Suitable surfactants for use in compositions according to the present invention include, for instance, anionic, nonionic, cationic and amphoteric surfactants or mixtures thereof.

Where usable, suitable anionic surfactants include alkali metal ($C_{12-18}$)alkyl sulphates, for instance sodium lauryl sulphate, and N-acyl sarcosinates and N-acyl taurines in which the acyl moiety has from 12 to 16 carbon atoms, for instance, N-lauroyl, N-myristoyl and N-palmitoyl sarcosine alkali metal salts.

Suitable nonionic surfactants include, for example, alkylpolyglucosides for instance the products marketed under the trade name 'Plantacare' by Henkel, polyethoxylated sorbitol esters, in particular polyethoxylated sorbitol monoesters, for instance, PEG(40) sorbitan di-isostearate, and the products marketed under the trade name 'Tween' by ICI; polycondensates of ethylene oxide and propylene oxide (poloxamers), for instance the products marketed under the trade name 'Pluronic' by BASF-Wyandotte; condensates of propylene glycol; polyethoxylated hydrogenated castor oil, for instance, cremophors; and sorbitan fatty esters.

Suitable amphoteric surfactants include, for example, long chain imidazoline derivatives such as the product marketed under the trade name 'Miranol C2M' by Miranol; long chain alkyl betaines, such as the product marketed under the tradename 'Empigen BB' by Albright+Wilson, and long chain alkyl amidoalkyl betaines, such as cocamidopropylbetaine, and mixtures thereof.

Suitable cationic surfactants include the D,L-2-pyrrolidone-5-carboxylic acid salt of ethyl-N-cocoyl-L-arginate, marketed under the trade name CAE by Ajinomoto Co. Inc., and cocamidopropyl PG dimonium chloride phosphate and lauramidopropyl PG dimonium chloride phosphate, available under the trade names Monaquat PTC and Monaquat PTL, respectively, from Mona Corporation.

Advantageously, the surfactant is present in the range 0.005 to 20%, preferably 0.1 to 10%, more preferably 0.1 to 5% by weight of the total composition.

Suitable thickening agents for gel or dentifrice formulations include, for instance, nonionic thickening agents such as, for example, $(C_{1-6})$alkylcellulose ethers, for instance methylcellulose; hydroxy$(C_{1-6})$alkylcellulose ethers, for instance hydroxyethylcellulose and hydroxypropylcellulose; $(C_{2-6})$alkylene oxide modified $(C_{1-6})$alkylcellulose ethers, for instance hydroxypropyl methylcellulose; and mixtures thereof. Other thickening agents such as natural and synthetic gums or gum like material such as Irish Moss, xanthan gum, gum tragacanth, sodium carboxymethylcellulose, polyvinyl pyrrolidone, starch and thickening silicas may also be used. Preferably the thickening agent is xanthan gum.

Advantageously the thickening agent is present in the range 0.01 to 30%, preferably 0.1 to 15%, more preferably 1 to 5%, by weight of the total composition.

Suitable humectants for use in compositions of the invention include for instance, glycerine, xylitol, sorbitol, propylene glycol or polyethylene glycol, or mixtures thereof; which humectant may be present in the range from 5 to 30%, preferably 5 to 20%, more preferably 5 to 15% by weight of the total composition.

A preferred humectant is xylitol which can enhance the remineralisation of teeth.

Suitable abrasives for use in dentifrice compositions of the present invention include calcium carbonate, calcium phosphates, calcium pyrophosphate, insoluble sodium metaphosphate, sodium aluminosilicate, alumina, hydrated alumina, zinc orthophosphate, plastic particles, and silica, of which silica is the preferred abrasive.

Suitable silicas include natural amorphous silicas, such as, for instance, diatomaceous earth, and synthetic amorphous silicas, such as precipitated silicas and silica gels, including silica xerogels. Suitable silica xerogels are described in U.S. Pat. No. 3,538,230. Suitable grades of precipitated silicas have BET surface areas in the range 20 to 300, preferably 20 to 100 $m^2/g$ and median agglomerate sizes in the range 2 to 50, preferably 5 to 30 m.

Suitable precipitated silicas and silica xerogels are those marketed under the trade names Sident and Syloblanc, by Degussa and W R Grace Corporation Davison Chemical Division, respectively.

Advantageously, the silica is a "low anion" silica. As used herein, the term "low-anion" silicas refers to those in which anionic impurities such as sodium sulphate and sodium silicate which normally arise during the course of the manufacturing process are kept to a minimum, through careful control of the manufacturing process. "Low anion" silicas suitably have less than 1%, preferably less than 0.5% advantageously less than 0.25% by weight of anionic impurities.

Suitable such "low anion" silicas are described in EP 0 368 130 (Proctor & Gamble), EP 0 315 503 and EP 0 396 459 (Rhone-Poulenc) and WO 90/05113 (J.M. Huber Corp). Alternatively, grades of commercially available silica with ionic impurities may be rendered suitable by washing thereof with deionised water. Conductivity measurements on the water after washing may be used to monitor the efficacy of such washing. Suitably the conductivity of the water after washing is reduced to less than 200 $\mu$Siemens/cm. Suitable "low anion" silicas include the grade RP93 available from Rhone-Poulenc.

Suitably, dentifrice compositions will have from 5 to 80%, preferably from 10 to 60% by weight of the abrasive.

The compositions according to the present invention may be prepared by admixing the ingredients in the appropriate relative amounts in any order that is convenient and thereafter and if necessary adjusting the pH to give the final desired value.

The present invention also provides a method of remineralising teeth which comprises administering an effective amount of a composition of the present invention to an individual in need thereof.

The compositions of the present invention may be applied to the teeth in standard manner after thorough mixing of the calcium and phosphate phases prior to use.

Such compositions may be applied from 1 to 4 times a day for sufficient time and in sufficient quantity to effect remineralisation of the teeth. For example one application may provide from 0.05 to 0.5 g of calcium ions and from 0.05 to 0.5 g of phosphate ions in a calcium to phosphate molar ratio of from 0.5:1 to 5:1 and may be kept in contact with the teeth for from 30 seconds to 30 minutes, preferably from 5 to 20 minutes, eg about 10 minutes.

Suitably a dentifrice or gel may be applied by means of a brush.

Suitably a rinse may be used as a mouthwash.

Preferably a gel may be applied to the teeth in a dental tray (one for each set of teeth) which preferably is formed to fit closely around an individual's teeth.

Similarly a rinse may be applied to the teeth in a dental tray which preferably contains a sponge to facilitate retention of the rinse composition in close contact with the teeth.

The invention is further illustrated by the following Examples.

EXAMPLE 1

A gel was made up as follows:

| | GEL | |
|---|---|---|
| Raw Material | Calcium-phase Amount | Phosphate-phase Amount |
| demin. water, boiled | 80.091 | 80.441 |
| Calciumchloride Dihydrate | 7.609 | — |
| Sodium Dihydrogenphosphate Monohydrate | — | 3.638 |
| Sodium Fluoride (1% Solution) | — | 0.221 |
| Sodium Polyphosphate (1% Solution) | — | 0.100 |
| Benzalkoniumchloride | 0.100 | 0.100 |
| Cremophor RH60 | 0.500 | 3.000 |
| Xylitol | 10.000 | 10.000 |
| Sodium Saccharin | 0.100 | 0.100 |
| Keltrol RD (Xanthan Gum) | 1.500 | 1.500 |
| Flavour | — | 0.400 |
| Flavour | — | 0.400 |
| On mixing the pH is 3.7 | pH 4,91 | pH 4,31 |

EXAMPLE 2

A rinse was made up as follows:

RINSE

| Raw Material | Calcium-phase Amount | Phosphate-phase Amount |
|---|---|---|
| demin. water, boiled | 81.691 | 80.941 |
| Calciumchloride Dihydrate | 7.609 | — |
| Sodium Dihydrogenphosphate Monohydrate | — | 3.638 |
| Sodium Fluoride (1% Solution) | — | 0.221 |
| Sodium Polyphosphate (1% Solution) | — | 0.100 |
| Benzalkoniumchloride | 0.100 | 0.100 |
| Cremophor RH60 | 0.500 | 4.100 |
| Xylitol | 10.000 | 10.000 |
| Sodium Saccharin | 0.100 | 0.100 |
| Keltrol RD (Xanthan Gum) | — | — |
| Flavour | — | 0.400 |
| Flavour | — | 0.400 |
| On mixing the pH is 3.7 | pH 5,23 | pH 4,33 |

EXAMPLE 3

A rinse was made up as follows:

RINSE

| Raw Material | Calcium-phase Amount | Phosphate-phase Amount |
|---|---|---|
| demin. water, boiled | ad100 | ad100 |
| Calciumchloride Dihydrate | 7.609 | — |
| Sodium Dihydrogenphosphate Monohydrate | — | 3.638 |
| Sodium Fluoride (1% Solution) | — | 0.221 |
| Sodium Polyphosphate (1% Solution) | — | 0.100 |
| Benzalkoniumchloride | 0.100 | 0.100 |
| Cremophor RH60 | 0.500 | 4.100 |
| Xylitol | 10.000 | 10.000 |
| Sodium Saccharin | 0.100 | 0.100 |
| Keltrol RD (Xanthan Gum) | 0.500 | 0.500 |
| Flavour | — | 0.400 |
| Flavour | — | 0.400 |
| On mixing the pH is 3.7 | pH 5,23 | pH 4,33 |

EXAMPLE 4

A dentifrice was made up as follows:

DENTIFRICE

| Raw Material | Calcium-phase Amount | Phosphate-phase Amount |
|---|---|---|
| Water, deionized, boiled | 51,691 | 54,101 |
| Calciumchloride Dihydrate | 7,609 | — |
| Sodium Dihydrogenphosphate Monohydrate | — | 3,638 |
| Sodium Polyphosphate | — | 0,001 |
| Glycerin | 20,000 | 20,000 |
| Sodium Saccharin | 0,200 | 0,200 |
| Sodium Monofluorophosphate | — | 1,560 |
| Hydrated Silica (Polishing Agent) | 10,000 | 10,000 |
| Hydrated Silica (Thickener) | 5,000 | 5,000 |
| Benzalkoniumchloride | 0,100 | 0,100 |
| Xanthan Gum | 1,500 | 1,500 |
| Sodium Methyl Cocoyl Taurate | 1,500 | 1,500 |
| PEG-60 Hydrogenated Castor Oil | 2,000 | 2,000 |
| Flavour | 0,400 | 0,400 |
| Mixing pH 3,5–4,0 | pH 5,0–6,0 | pH 5,0–6,0 |

EXAMPLE 5

A gel was made up as follows:

GEL

| Raw Material | Calcium-phase Amount | Phosphate-phase Amount |
|---|---|---|
| demin. water, boiled | 73.794 | 78.641 |
| Calcium Chloride Dihydrate | 4.317 | — |
| Calcium Lactate | 6.789 | — |
| Sodium Dihydrogenphosphate Monohydrate | — | 3.638 |
| Sodium Fluoride (1% Solution) | — | 0.221 |
| Sodium Polyphosphate (1% Solution) | — | 0.100 |
| Benzalkoniumchloride 50% Solution | 0.200 | 0.200 |
| Cremophor RH40 | 0.500 | 5.000 |
| Xylitol | 10.000 | 10.000 |
| Sodium Saccharin | 0.100 | 0.100 |
| Keltrol RD (Xanthan Gum) | 1.300 | 1.300 |
| Flavour | — | 0.400 |
| Flavour | — | 0.400 |
| 90% Lactic acid Solution | 3.00 | — |
| On mixing the pH is 3.5 | pH 3.10 | pH 4.31 |

EXAMPLE 6

METHOD FOR MEASURING REMINERALISATION

The remineralisation properties were measured on porous hydroxyapatite disks using a microradiography method.

As described previously (reference ORCA congress 1996, abstract no. 29, Cser, Wiedemann and Klinger) the porous hydroxyapatite disks (pore volume 53%, std. dev. 0.7%) are submitted to 4 cycles of mineralisation.

The cycles were run as follows:

2–20 minutes treatment with the innovative remineralisation product (REM-L), a pH increase to REM-H with a pH 6.5 solution of artificial saliva (1 mol Ca, 1 mol Phosphate, pH 6.5) (ramping time) and a stationery phase of up to 65 min.

The REM-profiles given in the examples read as follows:

2/0/63 or 20/0/40 meaning 2 minutes of REM-L, instanteous pH-change, 63 min. REM-H.

The mineral built-in was measured both gravimetrically and radiographically.

Results show good correlation of the gravimetric and radiographic results. Gravimetric result for the listed example 1 and example 3 are listed below.

Gravimetric results for example 1 (Gel):

| Remin. profile | 5/0/60 | 7.5/0/57.5 | 20/0/45 |
|---|---|---|---|
| mineral built-in (in mg) after 4 cycles | 0,8 mg | 1,02 mg | 1,7 mg | gravimetric results for example 2 (rinse):

| Remin. profile | 0,5/0/64.5 | 2/0/63 |
|---|---|---|
| mineral built-in (in mg) after 4 cycles | 1,4 mg | 1,9 mg |

I claim:

1. A two phase remineralising composition comprising:
   a) as a first component an aqueous calcium phase comprising a water-soluble calcium salt providing from 0.05 to 10%, by weight of the calcium phase, of calcium ions, and
   b) as a second component an aqueous phosphate phase comprising a stabilising amount of a polyphosphate salt and a water-soluble phosphate salt providing from 0.05 to 10%, by weight of the phosphate phase, of phosphate ions; the two phases being kept separate until use, whereupon on mixing they provide a single phase having a pH from 2.0 to 5.0 and a molar ratio of calcium ions to phosphate ions of from 0.5:1 to 5:1 capable of remineralising teeth.

2. A composition according to claim 1 wherein the calcium salt provides from 1 to 5%, by weight of the calcium phase, of calcium ions.

3. A composition according to claim 1 wherein the calcium salt is calcium chloride optionally in admixture with calcium lactate.

4. A composition according to claim 1 wherein the phosphate salt provides from 1 to 5% by weight of the phosphate phase, of phosphate ions.

5. A composition according to claim 1 wherein the polyphosphate salt is sodium polymetaphosphate.

6. A composition according to claim 1 wherein the pH of the calcium and phosphate phases are such that on mixing result in a pH from 3.5 to 4.0.

7. A composition according to claim 1 wherein the molar ratio of calcium ions to phosphate ions is from 1:1 to 3:1.

8. A composition according to claim 1 which further comprises a source of fluoride ions.

9. A composition according to claim 1 in the form of a rinse, gel or dentifrice.

10. A composition according to claim 1 which comprises xylitol.

11. A composition according to claim 1 which comprises xanthan gum.

12. A kit comprising separately packaged calcium and phosphate phases as defined in claim 1, which on mixing provide a single phase capable of remineralising teeth.

13. A method of remineralising teeth which comprises administering an effective amount of a composition according to claim 1 to an individual in need thereof.

* * * * *